(12) United States Patent
Edwards

(10) Patent No.: US 8,940,005 B2
(45) Date of Patent: Jan. 27, 2015

(54) LOCKING FLEXIBLE SURGICAL INSTRUMENTS

(75) Inventor: Kevin C. Edwards, Olive Branch, MS (US)

(73) Assignee: Gyrus ENT L.L.C., Bartlett, TN (US)

( * ) Notice: Subject to any disclaimer, the term of this patent is extended or adjusted under 35 U.S.C. 154(b) by 211 days.

(21) Appl. No.: 13/205,104

(22) Filed: Aug. 8, 2011

(65) Prior Publication Data

US 2013/0041392 A1 Feb. 14, 2013

(51) Int. Cl.
*A61B 17/32* (2006.01)
*A61B 17/3207* (2006.01)
*A61B 17/02* (2006.01)
*A61B 17/29* (2006.01)

(52) U.S. Cl.
CPC ..... *A61B 17/3207* (2013.01); *A61B 2017/0243* (2013.01); *A61B 2017/2905* (2013.01); *A61B 2017/2908* (2013.01); *A61B 2017/320032* (2013.01)
USPC .......................................................... 606/170

(58) Field of Classification Search
USPC .................. 606/79, 167, 169, 170, 171, 180; 294/102.1, 103.1; 81/64, 65.2, 68
See application file for complete search history.

(56) References Cited

U.S. PATENT DOCUMENTS

| | | | |
|---|---|---|---|
| 4,483,562 A | 11/1984 | Schoolman | |
| 4,646,738 A | 3/1987 | Trott | |
| 5,348,259 A * | 9/1994 | Blanco et al. | 248/276.1 |
| 5,527,325 A | 6/1996 | Conley et al. | |
| 5,620,415 A * | 4/1997 | Lucey et al. | 604/22 |
| 5,707,350 A | 1/1998 | Krause et al. | |
| 5,916,147 A * | 6/1999 | Boury | 600/146 |
| 6,139,563 A | 10/2000 | Cosgrove, III et al. | |
| 6,638,287 B2 | 10/2003 | Danitz et al. | |
| 6,656,195 B2 * | 12/2003 | Peters et al. | 606/159 |
| 6,758,808 B2 * | 7/2004 | Paul et al. | 600/229 |
| 7,247,161 B2 | 7/2007 | Johnston et al. | |
| 7,828,808 B2 | 11/2010 | Hinman et al. | |
| 2002/0099268 A1 | 7/2002 | Paul et al. | |
| 2002/0120178 A1 * | 8/2002 | Tartaglia et al. | 600/114 |
| 2004/0044350 A1 | 3/2004 | Martin et al. | |
| 2004/0138529 A1 * | 7/2004 | Wiltshire et al. | 600/144 |
| 2005/0273084 A1 * | 12/2005 | Hinman et al. | 606/1 |
| 2006/0058582 A1 * | 3/2006 | Maahs et al. | 600/144 |
| 2006/0074442 A1 | 4/2006 | Noriega et al. | |
| 2009/0093674 A1 * | 4/2009 | Adams | 600/104 |
| 2009/0270896 A1 | 10/2009 | Sullivan et al. | |
| 2010/0076451 A1 | 3/2010 | Zwolinski et al. | |
| 2010/0087711 A1 * | 4/2010 | Edwards | 600/139 |

OTHER PUBLICATIONS

Dictionary definition of "freely" from www.thefreedictionary.com.*
Dictionary definition of "compressed" from Merriam Webster.*
Dictionary definition of "compressed" from Merriam Webster. Aug. 23, 2010.*

(Continued)

*Primary Examiner* — Katherine M Shi
(74) *Attorney, Agent, or Firm* — Oliff PLC

(57) ABSTRACT

A flexible-shaft surgical instrument has a compression member that is distally movable to provide a compression force between the compression member and a distal compression bearing to compress a plurality of links and rigidly lock a semi-rigid tube formed by those links at any of a variety of user-selectable predetermined positions. The semi-rigid tube is configured to be bent and locked at the user-selectable predetermined position and, upon proximal movement of the compression member, returned to an unlocked state without significant plastic deformation of the semi-rigid tube.

20 Claims, 8 Drawing Sheets

(56) References Cited

OTHER PUBLICATIONS

Dictionary definition of "freely" from www.thefreedictionary.com. Jun. 21, 2005.*

Sep. 17, 2012 International Search Report issued in PCT/US2012/044201.
Sep. 17, 2012 Written Opinion issued in PCT/US2012/044201.

* cited by examiner

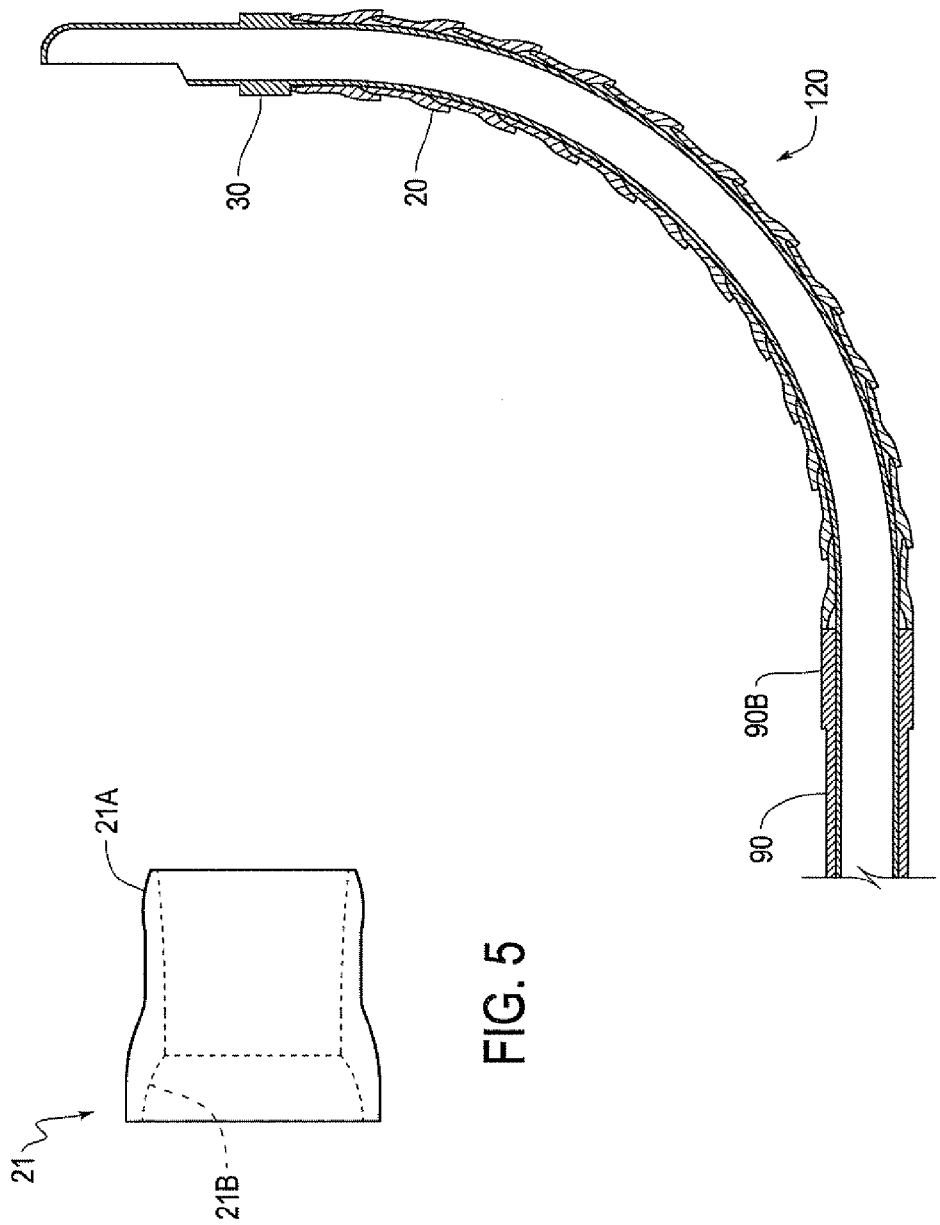

LOCKING FLEXIBLE SURGICAL INSTRUMENTS

BACKGROUND

This disclosure relates to surgical instruments having flexible portions that can be bent and locked into various orientations.

Surgical instruments with thin, elongated shafts for accessing various surgical sites through natural or surgical openings in the body are known. These surgical instruments may be provided with generally thin, elongated shafts in either straight or curved configurations.

Surgical instruments used to shave, cut, resect, abrade and/or remove tissue, bone and or other bodily materials are known. Such surgical instruments can include a cutting surface, such as a rotating blade, disposed on an elongated inner tube that is rotated within an elongated outer tube having a cutting window. The inner and outer tubes together form a surgical cutting blade. In general, the elongated outer tube includes a distal end defining an opening or cutting window that exposes the cutting surface of the inner tube (at the distal end of the inner tube) to tissue, bone and/or any other bodily materials. A powered handpiece is used to rotate the inner tube with respect to the outer tube while an outer tube hub (connected to the proximal end of the outer tube) is rigidly fixed to the handpiece and an inner tube hub (connected to the proximal end of the inner tube) is loosely held in place by the powered handpiece and can move axially.

In such surgical instruments, it is often useful, or even necessary, for a surgeon to be able to precisely orient a tip of the surgical cutting blade (defining the cutting surface within the cutting window) at a specific angle. Because of this requirement, it is known to provide kits having multiple surgical cutting blades having first ends angled to different fixed degrees. Thus, depending on the needs or requirements of the surgery, a surgeon can switch between multiple different surgical cutting blades multiple times during surgery so as to precisely orient the selected surgical cutting blade in the exact location he/she is trying to reach. However, providing kits having multiple surgical cutting blades having first ends angled to different fixed degrees can be expensive and, even with a variety of different angles, may result in the surgeon not having a particular desired configuration.

Locking flexible shaft devices are known. For example, U.S. Pat. No. 4,483,562 discloses a surgical device having a flexible shaft portion made up of a plurality of alternating spacers and spheres. U.S. Pat. No. 4,483,562 discloses that tension on a centrally disposed tensioning wire can be adjusted to rigidify the shaft portion. However, the configuration illustrated in U.S. Pat. No. 4,483,562 is not desirable in the context of some surgical instruments, such as microdebriders, which requires an inner hollow tube portion for removal of tissue, bone and/or any other bodily materials.

SUMMARY

User preferences, such as those of the surgeons, as well as the demands of surgery dictate limitless requirements for the curvature of a surgical instrument and for the orientation of the cutting window of the instrument relative to the curvature of the instrument. Accommodating such user preferences and surgery requirements during surgical procedures requires the use of many surgical instruments having different angled configurations and/or window orientations. The use of multiple surgical instruments can be very costly and requires hospitals/surgeons to come equipped with a large variety of surgical instruments so as to accommodate any and all needs that arise during surgery.

It would be advantageous to provide an instrument that would allow the surgeon to utilize one surgical cutting instrument (or blade) for all surgery requirements. Accordingly, it is desirable to provide a single surgical instrument that can be repeatedly bent and locked into various different desired angles and window orientations. The arrangement allows the surgeon to use one blade for many surgical applications without having the need to purchase, store and use large quantities of blade inventory to meet the demands of surgery.

In various embodiments, a flexible-shaft surgical instrument having a semi-rigid tube with a distal end and a proximal end may be provided. The semi-rigid tube may have a plurality of links, with the links having a male portion and a female portion. The male portion may be inserted into the female portion of an adjacent link. A surgical device having an elongated portion with a distal end, a proximal end and an intermediate portion between the distal and proximal ends may be provided. At least part of the intermediate portion may be flexible. At least part of the surgical device may be disposed within a hollow portion of the semi-rigid tube such that the plurality of links are aligned with at least part of the intermediate portion of the surgical device. A distal compression bearing may be provided on the surgical device at a position that is adjacent to the distal end of the surgical device. The distal compression bearing may radially protrude from an outer surface of the surgical device. A compression member that is movably attached to the surgical device at a position that is proximal to the proximal end of the semi-rigid tube may be provided. The semi-rigid tube may be disposed between the compression member and the distal compression bearing such that the distal end of the semi-rigid tube abuts the distal compression bearing. The compression member may be distally movable to provide a compression force between the compression member and the distal compression bearing to compress the plurality of links together and rigidly lock the semi-rigid tube and the intermediate portion of the surgical device at a user-selectable predetermined position. The semi-rigid tube may be configured to be bent and locked at the user-selectable predetermined position and, upon proximal movement of the compression member, returned to an unlocked state without significant plastic deformation of the semi-rigid tube. There would be a small amount of plastic deformation, but the function of the surgical device would not be compromised.

According to one embodiment, the plurality of adjacent links may be of a number and configuration large enough such that the semi-rigid tube and the intermediate portion of the surgical device may be bent between an angle of 0° and +/−110°. The allowable bend angle is scalable and is not limited to a range between 0° and +/−110°. That is, lower and higher maximum bend angles are easily integrated.

In some embodiments, at least one portion of the female portion of the plurality of adjacent links may overlap the male portion of the adjacent link that is inserted into the female portion.

In some embodiments, a protective sheath may cover at least the semi-rigid tube.

In some embodiments, the links may be formed of a material that is biocompatible. The links may be formed of a material that is not degraded by chemicals employed in a surgical procedure.

In some embodiments, the surgical device includes at least one hollow tube.

The surgical device may be one of a shaver, an illumination device, a vacuum tube, an endoscope, an observation device, a microdebrider, or an electro-surgical device.

In some embodiments, the links may be formed from a polymer material. The polymer material may be polyetherimide, although other materials are possible.

In some embodiments, the compression member may be a tube having internal threads that engage external threads provided adjacent to an outer surface of the surgical device such that, upon rotating the compression member, the compression member moves distally or proximally to either compress and rigidly lock the plurality of links at the user-selectable predetermined position or return to an unlocked state.

In some embodiments, an intermediate member may be disposed between the compression member and the proximal end of the semi-rigid tube to transfer the compression force from the compression member to the plurality of links.

Preferably, the semi-rigid tube is freely bendable in the unlocked state.

In accordance with one aspect of the invention, the surgical instrument is a cutting instrument having an inner tube having a distal end and a proximal end, the inner tube including a cutting surface at the distal end and a flexible portion located between the distal end and the proximal end. The instrument also includes an outer tube having a distal end and a proximal end, and the outer tube may include a cutting window at the distal end and a flexible portion located between the distal end and the proximal end. The inner tube may be disposed within the outer tube so as to align the cutting surface of the inner tube with the cutting window of the outer tube. A semi-rigid tube may be disposed around at least the flexible portion of the outer tube, the semi-rigid tube having a distal end and a proximal end. The semi-rigid tube may include a plurality of links disposed around at least the flexible portion of the outer tube, each of the links including a male portion and a female portion, and the male portion being insertable into the female portion of an adjacent link. A distal compression bearing may be provided on the outer tube at a position that is adjacent to the distal end of the outer tube. The distal compression bearing may radially protrude from an outer surface of the outer tube. A compression member that is movably attached to the outer tube at a position that is proximal to the proximal end of the semi-rigid tube may be provided. The semi-rigid tube may be disposed between the compression member and the distal compression bearing such that the distal end of the semi-rigid tube abuts the distal compression bearing. The compression member may be distally movable to provide a compression force between the compression member and the distal compression bearing to compress the plurality of links together and rigidly lock the semi-rigid tube, the outer tube and the inner tube at a user-selectable predetermined position. The semi-rigid tube may be configured to be bent and locked at the user-selectable predetermined position and, upon proximal movement of the compression member, returned to an unlocked state without significant plastic deformation.

BRIEF DESCRIPTION OF THE DRAWINGS

Various exemplary embodiments of the disclosed surgical instrument will be described in detail with reference to the following drawings in which:

FIG. 5 illustrates a cross-sectional view of one link of a plurality of links according to one embodiment;

FIG. 6 illustrates a simplified cross-sectional view according to one embodiment;

DETAILED DESCRIPTION OF EMBODIMENTS

The following embodiments illustrate examples of a flexible-shaft surgical instrument that may be bent and locked to a desired angle on demand by a user. Disclosed embodiments of the flexible-shaft surgical instrument may be repeatably bent and re-bent and locked into multiple different positions without significant (detrimental) plastic deformation of the flexible-shaft surgical instrument occurring in any of its bend portions. While the disclosed embodiments may refer specifically to a repeatably bendable surgical instrument such as a shaver blade surgical instrument (i.e., a microdebrider), this example is provided only as being illustrative of a surgical instrument which may gain special advantages based on the repeatably bendable configuration of a semi-rigid shaft portion according to this disclosure. It should be recognized, however, that a device including a semi-rigid tube according to this disclosure may find utility in supporting any manner of surgical instrument where, for example, access is gained to a target surgical site inside a patient's body via one or more natural openings in the patient's body and/or via one or more surgically-created openings. In this regard, specific disclosed examples of surgical instruments, and the use of specific terms to describe those instruments, should be considered as illustrative only, and not limiting.

Figure 1:
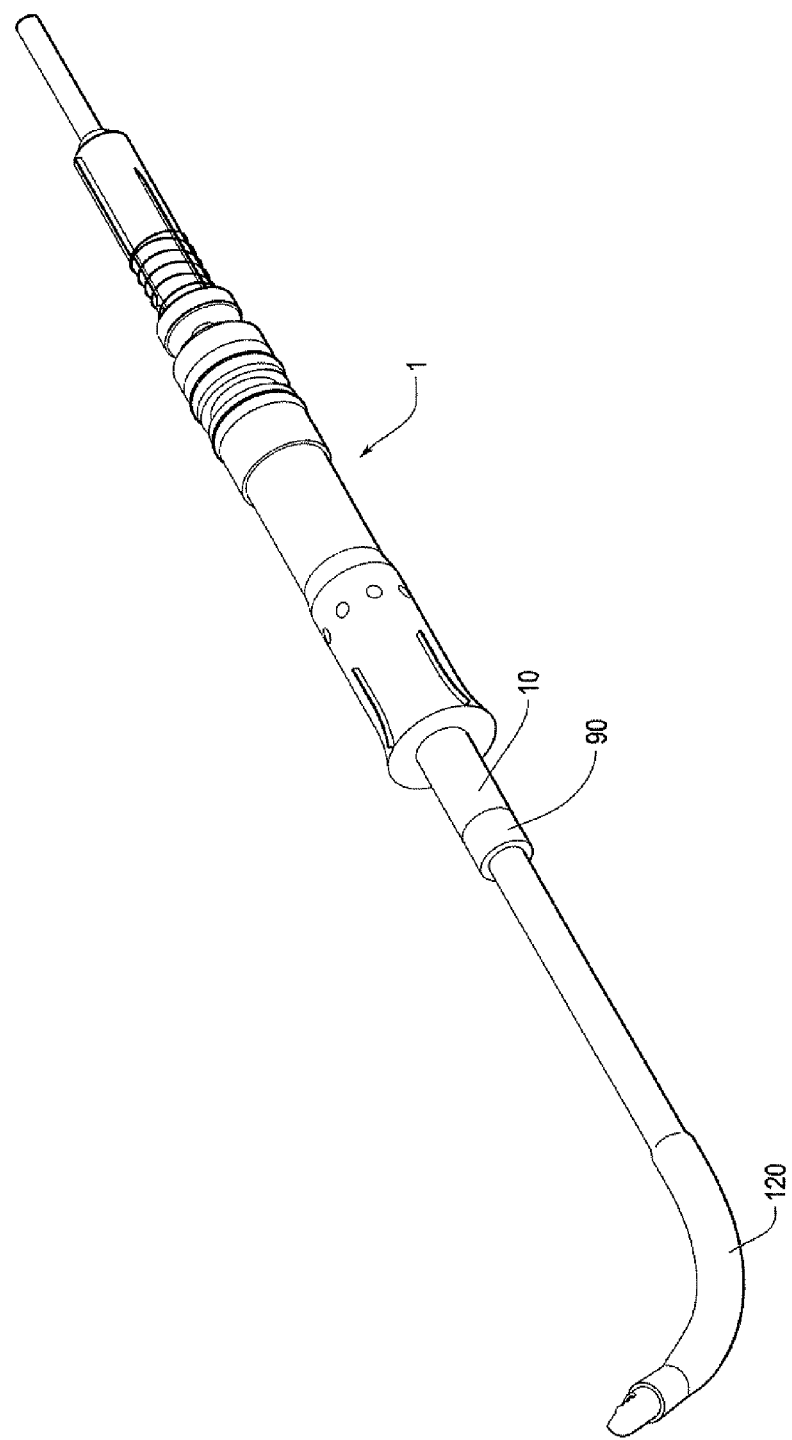
FIG. 1 illustrates a perspective view of a surgical instrument having a bent configuration.
Figure 2:
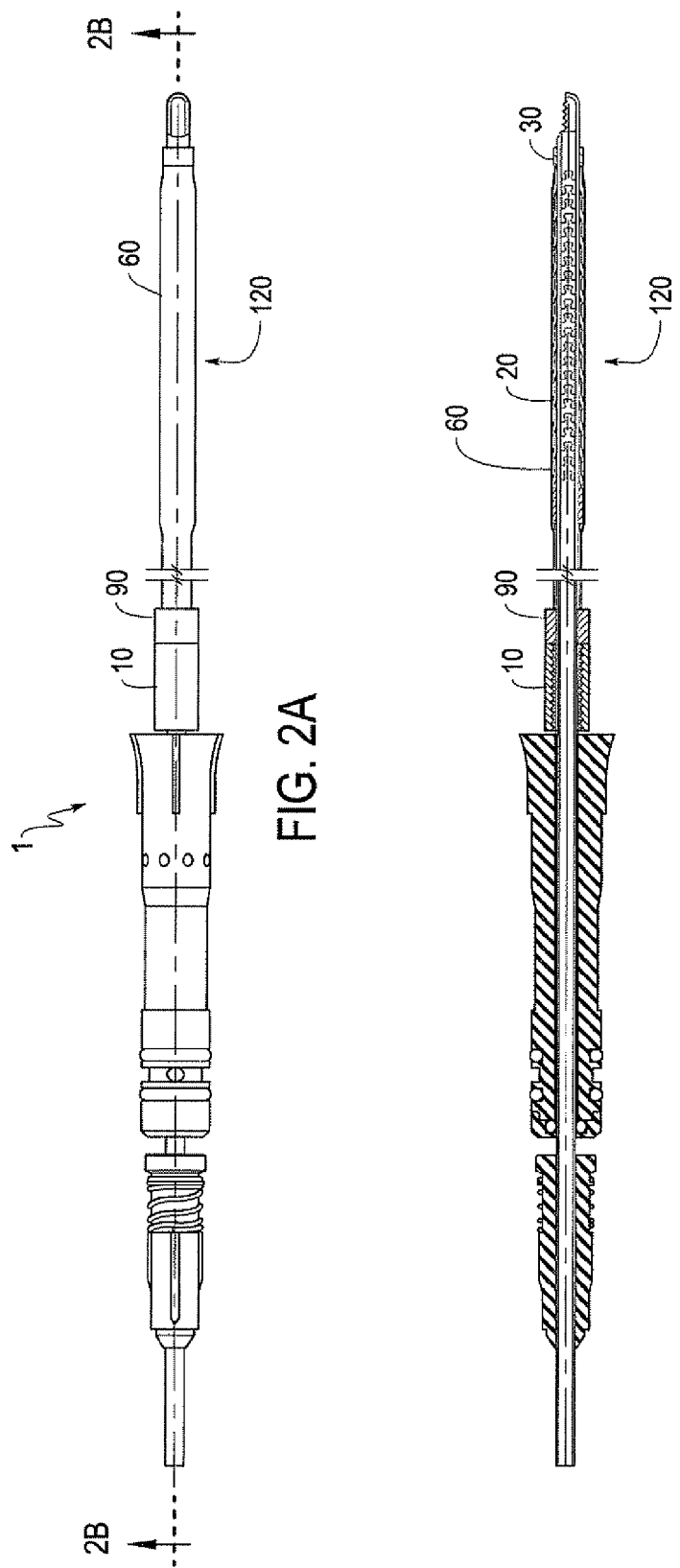
FIG. 2A illustrates a plan view of a surgical instrument having a straight configuration.
FIG. 2B illustrates a cross-sectional view taken along lines 2B-2B in FIG. 2A.
Figure 3:
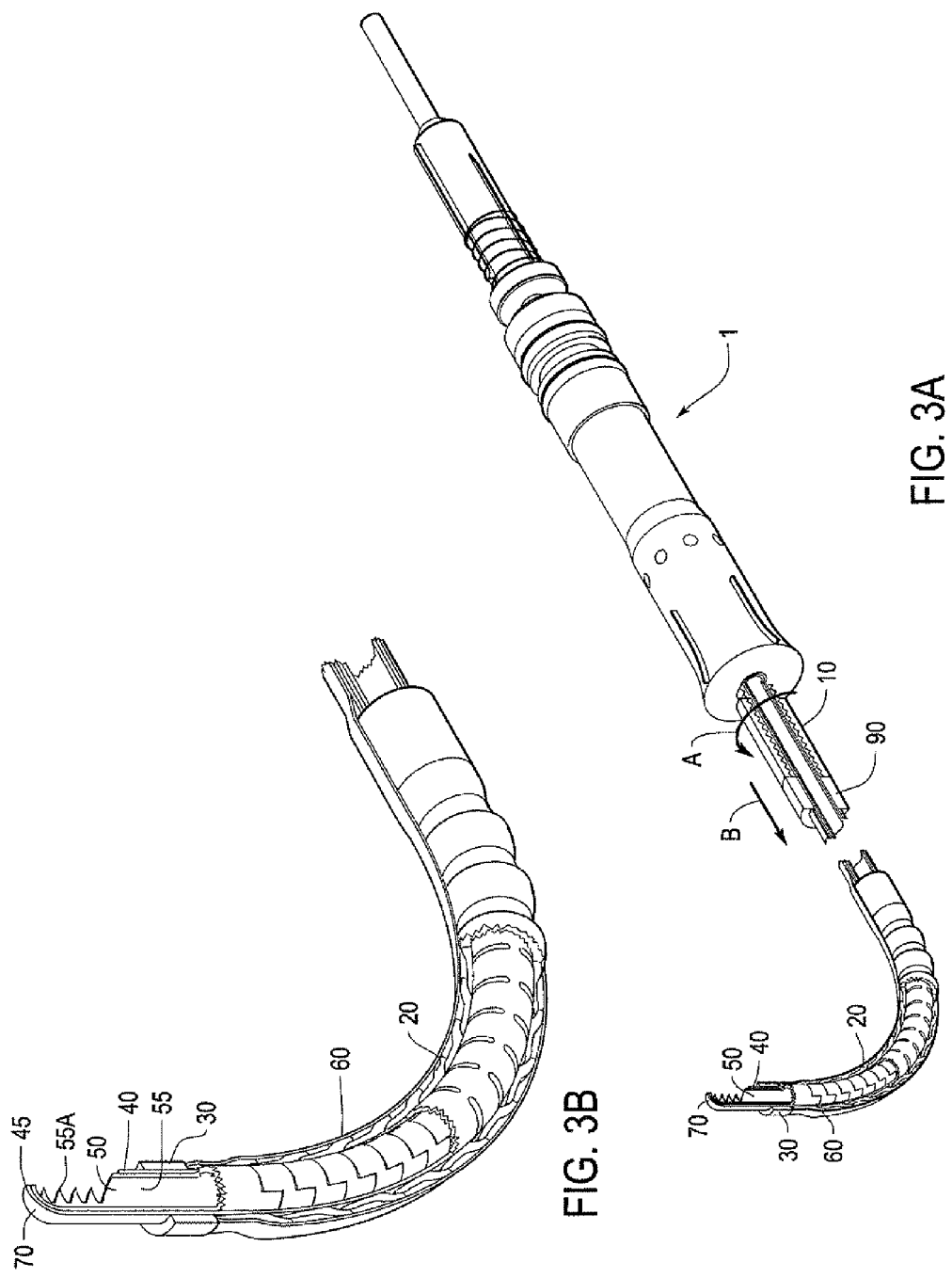
FIG. 3A illustrates a partial cross-sectional view of a surgical instrument having a bent configuration.
FIG. 3B illustrates an enlarged cross-sectional view of the bent portion illustrated in FIG. 3A.
Figure 4:
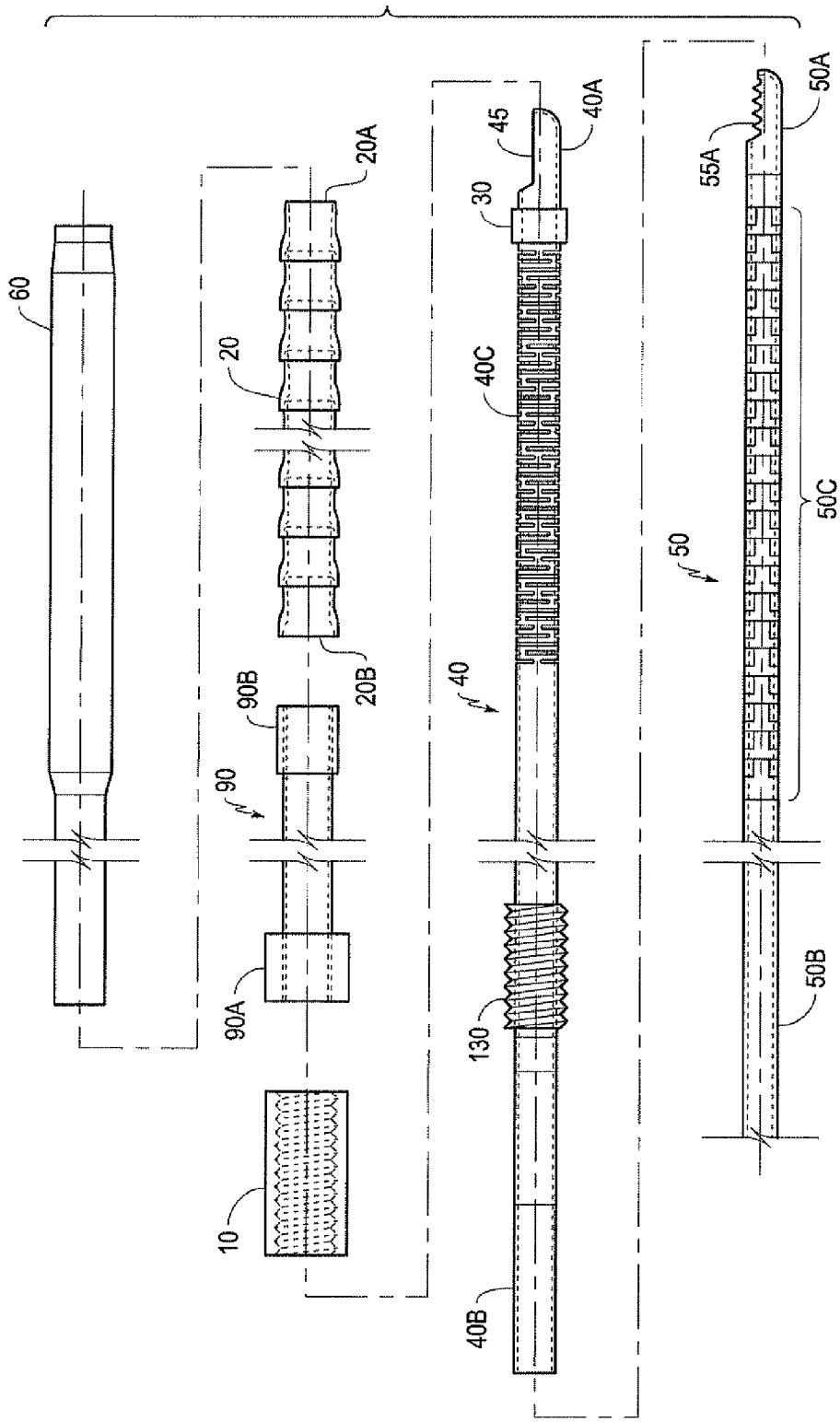
FIG. 4 illustrates an exploded view of the various layers of a portion of the surgical instrument according to one embodiment.

FIG. 1 illustrates one embodiment of a surgical instrument 1 having a bent configuration to be used in a powered surgical tool system. Except for the cutting tool, to be described hereafter, the system may be in accordance with the system disclosed in U.S. Pat. No. 7,247,161, the disclosure of which is incorporated herein by reference in its entirety. The shaft portion 120 of the surgical instrument 1 has a distally located semi-rigid section. FIGS. 2A and 2B illustrates the surgical instrument 1 while in a straight configuration, with FIG. 2B being a sectional view taken along lines 2B-2B in FIG. 2A. FIG. 3A illustrates a cross-sectional view of the surgical instrument 1 with an inner tube 50 co-axially disposed within an outer tube 40. FIG. 3B is an enlarged view of a distal end 70 of surgical instrument 1. The inner tube 50 includes a fluid/bodily materials removal passage 55 that extends the length of the inner tube 50. Passage 55 is attached to a suction source to remove fluids therethrough. The inner tube 50 also includes a cutting surface 55A at its distal end 50a (see FIG. 4) while the outer tube 40 includes a cutting window 45 at its distal end 40A (FIG. 4). The inner tube 50 is co-axially disposed within the outer tube 40 such that the cutting surface 55A is exposed at the cutting window 45. The cutting surface 55A disposed within the cutting window 45 form a cutting instrument, which cuts by rotating the inner tube 50 within the outer tube 40 while suction is applied through the inner tube 50. In particular, the embodiment illustrated in FIG. 1 is a surgical shaver or microdebrider, for use in endoscopic surgical procedures, that drives an elongated rotatable surgical instrument and aspirates material from a surgical work site. In operation, a surgeon grasps an elongated body of a handpiece in a manner similar to gripping a writing apparatus, such as a pencil or pen. While gripping the body of the handpiece in this manner, the surgeon is able to direct the distal end of the shaver blade assembly to the bodily material to be cut. With the tips of the surgeon's fingers, the surgeon can manipulate the shaft portion 120 to orient the cutting window 45 to an appropriate position to cut the bodily material.

Figure 9:
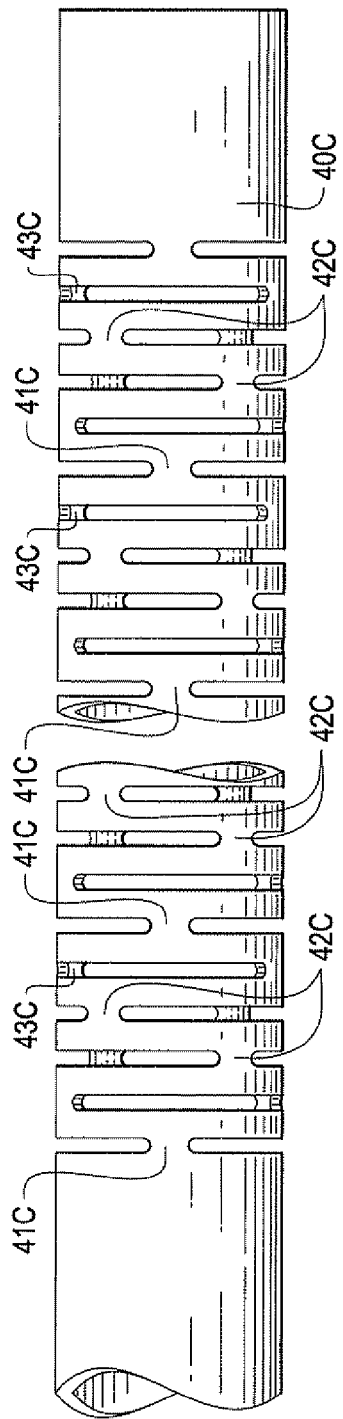
FIG. 9 illustrates one embodiment of a flexible portion having intermittent helically-staggered cuts.
Figure 10:
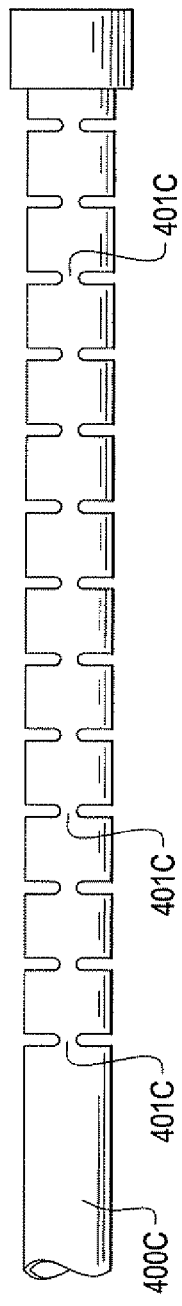
FIG. 10 illustrates another embodiment of a flexible portion having equally spaced cuts.

FIG. 4 illustrates an expanded view of the shaft portion 120 of the surgical instrument 1 according to one embodiment, including all of the various layers. As mentioned above, the inner tube 50 is provided with a distal end 50A having a cutting surface 55A and a proximal end 50B with a flexible portion 50C disposed therebetween. The outer tube 40 also includes a distal end 40A and a proximal end 40B with a flexible portion 40C disposed therebetween. The flexible portion 40C may comprise intermittent helically-staggered cuts through a wall of the outer tube 40 to allow the flexible portion 40C to bend in a number of planes. The intermittent helically-staggered cuts may be made with a laser or any other suitable means of cutting the flexible portion 40C. FIG. 9 is an enlarged view of the flexible portion 40C. The helically-staggered cuts illustrated in FIG. 9 allow for multi-plane bending. For example, as seen in FIG. 9, portions 41C provide a band of material for bending in a plane of the page, portions 42C provide a band of material for bending in a plane that is at 45° between the plane of the page and directly out of the page, and portions 43C provide a band of material for a bend plane that is out of the page. FIG. 10 illustrates another embodiment of a flexible portion 400C in which the spacing, width and depth of the cuts define the bend angle and radius. A continuous band of material 401C is provided along an axis that is orthogonal to the bend plane. The flexible portion 400C differs from the flexible portion 40C in that the flexible portion 400C only bends in one plane that is parallel to the surface of the page. Various structures can be used to make the flexible portions of the inner tube 50 and the outer tube 40. See, for example, U.S. Pat. No. 5,707,350 and U.S. Pat. No. 4,646,738, the disclosures of which are incorporated herein by reference in their entirety. A threaded portion 130 is provided proximally on the outer tube 40. The externally threaded portion 130 is configured to engage internal threads provided on a compression member 10. A distal compression bearing 30 is provided on a distal portion of the outer tube 40. As seen in FIG. 4, the distal compression bearing 30 is provided on an outer surface of the outer tube 40 such that the distal compression bearing 30 defines a radially extending protrusion. Compression bearing 30 could be formed as a one-piece structure of the outer tube 40 or it could be a separate piece fixed to outer tube 40.

An intermediate member 90 having a proximal end 90A and a distal end 90B is provided adjacent to the compression member 10. A semi-rigid tube 20 having a distal end 20A and a proximal end 20B is provided adjacent to the intermediate member 90. The outer tube 40 is provided coaxially within the compression member 10, the intermediate member 90 and the semi-rigid tube 20. When all of the parts of the surgical instrument 1 are combined, the flexible portions 40C, 50C and the semi-rigid tube 20 are aligned so as to form a flexible portion. A protective sheath 60 is preferably provided so as to cover at least the semi-rigid tube 20. The protective sheath 60 can be made of any material suitable to withstand repeated bending. Preferably the protective sheath 60 is made of a biocompatible polymer. In an alternative embodiment, the intermediate portion 90 may be omitted such that the compression member 10 directly contacts (abuts) against the proximal end 20B of the semi-rigid tube 20. The intermediate portion 90 is provided as a rigid spacer, such that fewer links may be used. In an embodiment where the intermediate portion 90 is not included, more links 21 may be provided such that the compression member 10 directly contacts the proximal end 20B of the semi-rigid tube 20, or the compression member 10 may be positioned closer to the semi-rigid tube 20.

In the embodiment illustrated in FIG. 4, the semi-rigid tube 20 includes a plurality of links 21 (see FIG. 5) that form a repeatably bendable structure. Each of the links 21 may be formed from a biocompatible polymer material such as polyetherimide ("PEI"). PEI is preferred. Other rigid, biocompatible polymers may be used, such as polycarbonate or PEEK may be used. Additionally, stainless steel, titanium or similar medical-grade metals may be used. PEI is preferred due to cost and the factors mentioned below. Each link 21 comprises a male portion 21A inserted into a female portion 2113 of an adjacent link 21 such that the female portion 21B overlaps the male portion 21A of an adjacent link 21. Of course, it is possible to omit or modify the female portion of the most proximal link 21 (the one contacting the intermediate member 90), and it is possible to omit or modify the male portion of the most distal link 21 (the one contacting compression bearing 30). Similarly, dedicated end pieces (instead of links) could be provided at the distal and/or proximal ends of the semi-rigid tube 20.

Examples of biocompatible materials include, for example, various metals, polymers, or the like, such as PEI, as mentioned above. PEI is commercially available, for example, under the trademark Ultem 1000®. PEI materials are favorable in flexible-shaft surgical instruments because materials such as PEI are approved for use in medical devices. Additional advantages are that these materials can be more easily formed to desired structures by varying processes such as machining or injection molding, than other biocompatible materials such as certain metals. These materials are also non-conductive, have relatively high strength, are elastically expandable without fracturing or plastic deformation, have high wear resistance, and are rated for high temperature use, making them autoclavable. Rating for high temperature use is important so that the flexible-shaft surgical instrument may survive multiple sterilizations and be re-used a plurality of times without adversely affecting the structural integrity of the bendable portions.

PEI is particularly advantageous because it is also creep resistant. Creep is an inherent condition of certain plastics and polymers where the strength of the material is gradually lost over time if the material is repeatedly or consistently exposed to a loading or bending force. Loading and bending forces would be present in exemplary embodiments such as those described here including press fit links. Other typical biocompatible polymers are less creep resistant and would thus have a shorter shelf life if used according to the exemplary embodiments. Because PEI is creep resistant, the shelf life may exceed that of typical biocompatible polymers if used according to the exemplary embodiments. However, because the device would likely be stored in the uncompressed, or unlocked, state, the links would probably not be susceptible to creep while stored. When assembled, parts using PEI are under a load condition that exhibits stresses on the assembled parts, which may tend to promote deformation from creeping. PEI is also non-reactive to most chemicals found in surgical procedures.

The surgical instrument 1 is configured to repeatedly transition from an unlocked state in which the shaft portion is easily bendable, to a locked state in which the shaft portion is rigidly set to a predetermined angle or configuration based on the actuation of the compression member 10. The predetermined angle or configuration can be any angle or configuration that a surgeon may desire for a given surgical procedure (or portion of a surgical procedure) and is not limited to a set number of predetermined angles. For example, using the same surgical instrument 1, the surgeon could adjust the bend angle to 30° for one part of a surgical procedure, and to 45° for another part of the same surgical procedure. An S-shaped, or bayonet-shaped, bend is also possible if the allowable bend length is long enough. In particular, in the embodiment illustrated, for example, in FIG. 3A, the compression member 10 compresses and locks the shaft portion 120 at a desired angle by being rotated in the direction of the arrow A. This rotation in the direction of arrow A causes the compression member 10 and the intermediate member 90 to be moved distally in the direction of arrow which causes at least the proximal-most link (the link at the proximal end 20B) of the semi-rigid tube 20 to move distally. In so doing, the semi-rigid tube 20 is compressed against the distal compression bearing 30, thereby locking the shaft portion 120 at a predetermined desired angle. To unlock the shaft portion 120, the compression member 10 may be rotated in a direction opposite that of arrow A in FIG. 3A. Rotation in the direction opposite that of arrow A in FIG. 3A causes tension between the plurality of links 21 of the semi-rigid tube 20 to be released such that the shaft portion 120 is freely bendable. The compression member 10 illustrated in the embodiment in FIG. 3A comprises a rotatably threaded configuration. However, any other means of urging plurality of links 21 of the semi-rigid tube 20 together is within the scope of the invention. With the surgical instrument 1, a surgeon can bend and lock the shaft portion 120 to virtually any desired orientation depending on the procedure to be performed, and the cutting window 45 orientation desired. Afterward, the surgeon can unlock the shaft portion and bend the shaft portion 120 to a different desired position to thereby adjust the bend angle and/or the orientation of the cutting window 45.

FIG. 6 illustrates a simplified view of the shaft portion 120 without the protective sheath 60 and without the inner tube 50. As seen in FIG. 6, the intermediate member 90 abuts the semi-rigid tube 20, which in turn abuts the distal compression bearing 30.

Figure 7A:
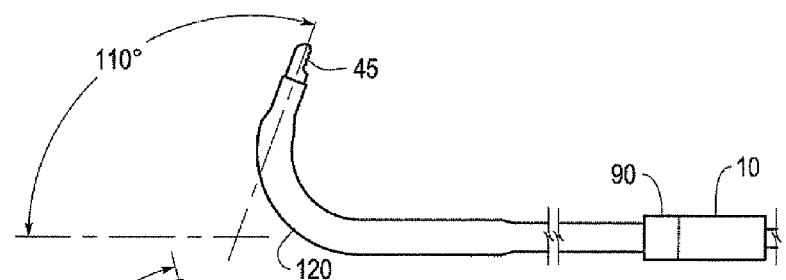
FIGS. 7A-F illustrate some examples of different bend angles that are possible with the surgical instrument.
Figure 7B:
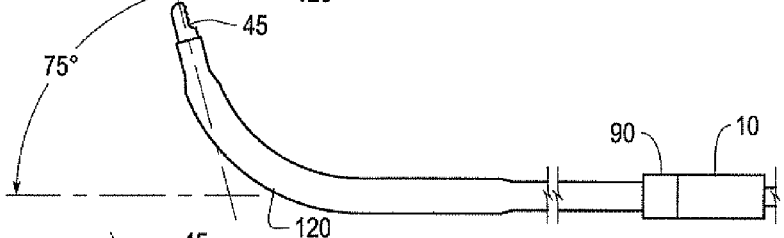
Figure 7C:
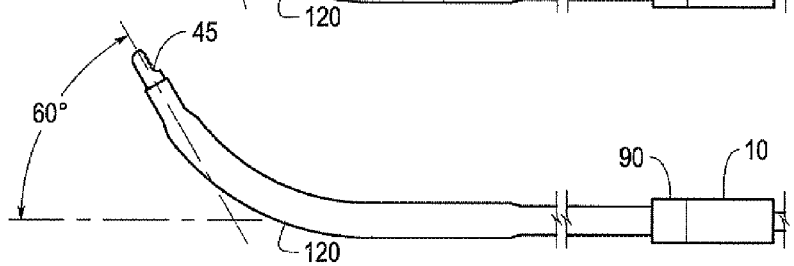
Figure 7D:
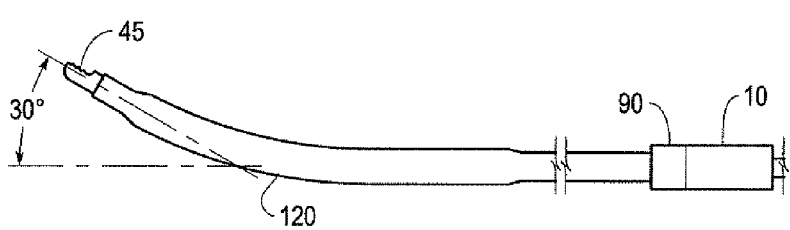
Figure 7E:
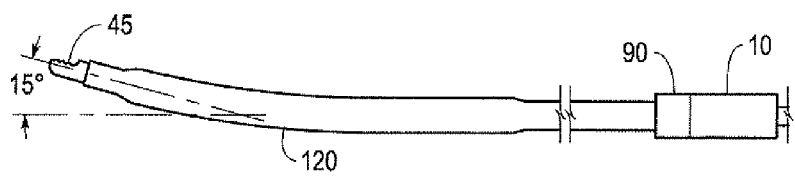
Figure 7F:
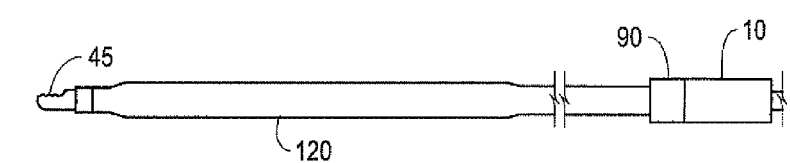

FIGS. 7A-F illustrate various different bend angles (including no bend (0°) in FIG. 7F) that are possible with the surgical apparatus 1. For example, the shaft portion 120 can be locked into a straight configuration (0°), or can be locked at a 15°, 30°, 60°, 75° or 110° angle. The various angles illustrated in FIGS. 7A-F are by no means exhaustive of the number of angles possible as the shaft portion 120 can be bent and locked in numerous other directions and at many other different angles. There are an infinite number of bend-angle/window orientations possible. For example, FIGS. 7A-E only illustrate the distal end of the surgical apparatus bending upward. However, the surgical apparatus can also bend downward at a −15°, −30°, −60°, −75° or −110° angle. The bending also can include a component of bend into or out of the page, and is not limited to bending within a single plane.

Figure 8:
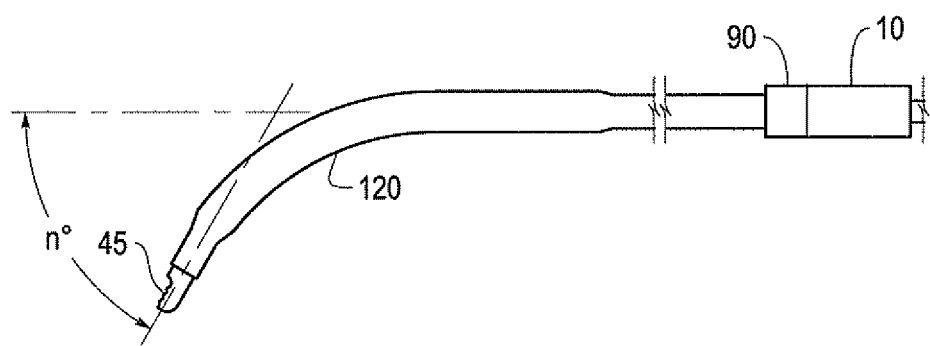
FIG. 8 illustrates a further example of a different bend angle and cutting window orientation that is possible with the surgical instrument.

FIG. 8 illustrates the shaft portion being bent at a −60° angle. As compared to FIG. 7C, in which the cutting window 45 is oriented inwardly, in FIG. 8, the cutting window 45 is oriented outwardly. Thus, the orientation of the cutting window 45 can be varied depending on the direction in which the shaft portion 120 is bent. Further, the shaft portion 120 may also be bent in a direction into or out of the page, or even a combination of different directions to achieve a desired bend-angle/window orientation. The extent to which the shaft portion can be bent depends on the arrangement of the cuts provided in the flexible portion 40C.

By providing the disclosed compression-type locking semi-rigid tube 20, the links 21 (and thus the semi-rigid tube 20) can be made thinner. This enables the outer diameter of the entire surgical instrument to be reduced, which makes the instrument cause less trauma on the patient. Without the compression-type locking structure, the links need to be made thicker so as to be stronger and thereby fit together (in a press-fit or interference-fit arrangement) more tightly so as to maintain any shape into which the tube is bent. Even then, such thicker, stiffer bendable tubes do not always stay in the bent orientation when being inserted into a patient. Thus, the disclosed embodiment provides a semi-rigid tube 20 made from thinner links and having a smaller outer diameter while also providing a stiffer tube when it is locked into the user-selected predetermined orientation.

The illustrated exemplary embodiments of the surgical tool as set forth above are intended to be illustrative and not limiting. Various changes may be made without departing from the spirit and scope of the invention.

What is claimed is:

1. A flexible-shaft surgical instrument comprising:
a semi-rigid tube having a distal end and a proximal end, the semi-rigid tube comprising (i) a distal-most link, (ii) a proximal-most link and (iii) a plurality of intermediate links disposed between the distal-most link and the proximal-most link, each of the plurality of intermediate links including a male portion and a female portion, the male portion being inserted into the female portion of an adjacent link;
a surgical device having an elongated portion with a distal end, a proximal end and an intermediate portion between the distal and proximal ends, at least part of the intermediate portion being flexible, at least part of the surgical device being disposed within a hollow portion of the semi-rigid tube such that at least some of the plurality of intermediate links are aligned with at least part of the intermediate portion of the surgical device;
a distal compression ring that is provided on the surgical device at a position that is adjacent to the distal end of the surgical device, the distal compression ring radially protruding from an outer surface of the surgical device; and
a compression member that is movably attached to the surgical device at a position that is proximal to the proximal end of the semi-rigid tube, the semi-rigid tube being disposed between the compression member and the distal compression ring, the compression member being distally movable relative to the surgical device to apply a compressive force to the semi-rigid tube that causes at least the proximal-most link to move distally and that presses the semi-rigid tube against the distal compression ring to urge the plurality of links together and rigidly lock the semi-rigid tube and the intermediate portion of the surgical device at a user-selectable predetermined bend angle, the compression member being proximally movable to release the compressive force from the semi-rigid tube and thereby return the semi-rigid tube and the intermediate portion of the surgical device to an unlocked state.

2. The surgical instrument of claim 1, wherein the plurality of adjacent links is of a number and configuration large enough such that the semi-rigid tube and the intermediate portion of the surgical device may be bent between an angle of 0° and at least +/−110°.

3. The surgical instrument of claim 1, wherein at least one portion of the female portion of the plurality of adjacent links overlaps the male portion of the adjacent link that is inserted into the female portion.

4. The surgical instrument of claim 1, further comprising a protective sheath covering at least the semi-rigid tube.

5. The surgical instrument of claim 1, wherein the links are comprised of a material that is biocompatible.

6. The surgical instrument of claim 1, wherein the links are comprised of a material that is not degraded by chemicals employed in a surgical procedure.

7. The surgical instrument of claim 1, wherein the surgical device includes at least one hollow tube.

8. The surgical instrument of claim 1, wherein the surgical device is one of a shaver, an illumination device, a vacuum tube, an endoscope, an observation device, a microdebrider, or an electro-surgical device.

9. The surgical instrument of claim 1, wherein the links are formed from a polymer material.

10. The surgical instrument of claim 9, wherein the polymer material is polyetherimide.

11. The surgical instrument of claim 1, wherein the compression member is a tube having internal threads that engage external threads provided adjacent to an outer surface of the surgical device such that, upon rotating the compression member, the compression member moves distally or proximally to either compress and rigidly lock the plurality of links at the user-selectable predetermined position or return to the unlocked state.

12. The surgical instrument of claim 1, further comprising:
an intermediate member disposed between the compression member and the proximal end of the semi-rigid tube.

13. The surgical instrument of claim 1, wherein, in the unlocked state, the semi-rigid tube is freely bendable.

14. The surgical instrument of claim 1, wherein the surgical device includes, at the distal end of the elongated portion, one of a cutting blade, a light-emitting portion, a suction aperture, an observation unit, and an electro-surgical energy applicator.

15. A surgical cutting instrument comprising:
an inner tube having a distal end and a proximal end, the inner tube including a cutting surface at the distal end and a flexible portion located between the distal end and the proximal end;
an outer tube having a distal tip and a proximal tip, the outer tube being hollow and including a cutting window at the distal tip and a flexible portion located between the distal tip and the proximal tip, the inner tube being disposed within the outer tube so as to align the cutting surface of the inner tube with the cutting window of the outer tube;
a semi-rigid tube disposed around at least the flexible portion of the outer tube and having a distal end and a proximal end, the semi-rigid tube comprising (i) a distal-most link, (ii) a proximal-most link and (iii) a plurality of intermediate links disposed between the distal-most link and the proximal-most link, at least some of the intermediate links being disposed around at least the flexible portion of the outer tube, each of the intermediate links including a male portion and a female portion, the male portion being insertable into the female portion of an adjacent link;
a distal compression bearing that is provided on an outer surface of the outer tube at a position that is adjacent to the distal tip of the outer tube, the distal compression bearing radially protruding from the outer surface of the outer tube; and
a compression member that is movably attached to the outer surface of the outer tube at a position that is proximal to the proximal end of the semi-rigid tube, the semi-rigid tube being disposed between the compression member and the distal compression bearing, the compression member being distally movable relative to the outer tube to apply a compressive force to the semi-rigid tube that causes at least the proximal-most link to move distally along the outer surface of the outer tube and that presses the semi-rigid tube against the distal compression bearing to urge the plurality of links together and rigidly lock the semi-rigid tube, the outer tube and the inner tube at a user-selectable predetermined bend angle, the compression member being proximally movable to release the compressive force from the semi-rigid tube and thereby return the semi-rigid tube, the outer tube and the inner tube to an unlocked state.

16. The surgical cutting instrument of claim 15, wherein the compression member is a tube having internal threads that engage external threads provided on an outer surface of outer tube such that, upon rotating the compression member, the compression member moves distally or proximally to either compress the plurality of links and rigidly lock the semi-rigid tube and the outer and inner tubes at the user-selectable predetermined position or return to the unlocked state.

17. The surgical cutting instrument of claim 15, further comprising an intermediate member disposed between the compression member and the plurality of links.

18. The surgical cutting instrument of claim 15, wherein the flexible portion of the outer tube comprises intermittent helically-staggered cuts through the wall of the outer tube to enable the outer tube to bend in multiple planes.

19. The surgical cutting instrument of claim 15, further comprising a protective sheath covering at least the plurality of links.

20. The surgical cutting instrument of claim 15, wherein the plurality of adjacent links is of a number and configuration large enough such that the outer tube and the inner tube may be bent between an angle of 0° and at least +/−110°.

* * * * *